United States Patent
Cai et al.

(10) Patent No.: US 12,037,627 B2
(45) Date of Patent: Jul. 16, 2024

(54) LACTOBACILLUS PARACASEI AND USES THEREOF

(71) Applicant: CHINA NATIONAL RESEARCH INSTITUTE OF FOOD & FERMENTATION INDUSTRIES CO., LTD., Beijing (CN)

(72) Inventors: Muyi Cai, Beijing (CN); Ruizeng Gu, Beijing (CN); Jun Lu, Beijing (CN); Kong Ling, Beijing (CN); Lu Lu, Beijing (CN); Ming Zhou, Beijing (CN); Xinyue Cui, Beijing (CN); Xingchang Pan, Beijing (CN); Zhe Dong, Beijing (CN); Yong Ma, Beijing (CN); Yaguang Xu, Beijing (CN); Yongqing Ma, Beijing (CN); Liang Chen, Beijing (CN); Ying Wei, Beijing (CN); Haixin Zhang, Beijing (CN); Yan Liu, Beijing (CN); Kelu Cao, Beijing (CN); Jing Wang, Beijing (CN); Guoming Li, Beijing (CN); Yuchen Wang, Beijing (CN); Yuqing Wang, Beijing (CN); Yuan Bi, Beijing (CN); Xiuyuan Qin, Beijing (CN)

(73) Assignee: CHINA NATIONAL RESEARCH INSTITUTE OF FOOD & FERMENTATION INDUSTRIES CO., LTD., Beijing (CN)

( * ) Notice: Subject to any disclaimer, the term of this patent is extended or adjusted under 35 U.S.C. 154(b) by 451 days.

(21) Appl. No.: 17/364,632

(22) Filed: Jun. 30, 2021

(65) Prior Publication Data
US 2021/0324428 A1 Oct. 21, 2021

Related U.S. Application Data

(63) Continuation of application No. PCT/CN2019/076376, filed on Feb. 27, 2019.

(30) Foreign Application Priority Data

Jan. 4, 2019 (CN) .......................... 201910008854.7

(51) Int. Cl.
  C12P 7/56 (2006.01)
  C12N 1/20 (2006.01)
  C12P 7/46 (2006.01)
  C12P 7/48 (2006.01)
  C12P 7/52 (2006.01)
  C12P 7/54 (2006.01)
  C12R 1/225 (2006.01)

(52) U.S. Cl.
  CPC ................ *C12P 7/56* (2013.01); *C12N 1/205* (2021.05); *C12P 7/46* (2013.01); *C12P 7/48* (2013.01); *C12P 7/52* (2013.01); *C12P 7/54* (2013.01); *C12R 2001/225* (2021.05)

(58) Field of Classification Search
CPC ...... C12P 7/56; C12P 7/46; C12P 7/48; C12P 7/52; C12P 7/54; C12P 7/40; C12N 1/205; C12N 1/20; C12R 2001/225
See application file for complete search history.

(56) References Cited

FOREIGN PATENT DOCUMENTS

| CN | 102669658 A | * | 9/2012 |
| CN | 103060243 A | | 4/2013 |
| CN | 108441436 A | | 8/2018 |
| JP | 5893772 B1 | | 3/2016 |

OTHER PUBLICATIONS

Peerajan, Sartjin, et al. "Enrichment of nutritional value of Phyllanthus emblica fruit juice using the probiotic bacterium, Lactobacillus paracasei HII01 mediated fermentation." Food Science and Technology 36 (2016): 116-123. (Year: 2016).*
Torrea, Diego, et al. "Comparison of inorganic and organic nitrogen supplementation of grape juice—Effect on volatile composition and aroma profile of a Chardonnay wine fermented with *Saccharomyces cerevisiae* yeast." Food chemistry 127.3 (2011): 1072-1083. (Year: 2011).*
Nagpal, Ravinder, Ashwani Kumar, and Manoj Kumar. "Fortification and fermentation of fruit juices with probiotic lactobacilli." Annals of microbiology 62 (2012): 1573-1578. (Year: 2012).*
Tee, Zhao Kang, et al. "Preeminent productivity of 1, 3-propanediol by Clostridium butyricum JKT37 and the role of using calcium carbonate as pH neutraliser in glycerol fermentation." Bioresource technology 233 (2017): 296-304. (Year: 2017).*
Seifan, Mostafa, Ali Khajeh Samani, and Aydin Berenjian. "New insights into the role of pH and aeration in the bacterial production of calcium carbonate (CaCO 3)." Applied microbiology and biotechnology 101 (2017): 3131-3142. (Year: 2017).*
Thiennimitr, Parameth, et al. "Lactobacillus paracasei HII01, xylooligosaccharides, and synbiotics reduce gut disturbance in obese rats." Nutrition 54 (2018): 40-47. (Year: 2018).*
Remel, chrome-extension://efaidnbmnnnibpcajpcglclefindmkaj/ https://assets.fishersci.com/TFS-Assets/LSG/manuals/IFU454061.pdf, Feb. 15, 2010 (Year: 2010).*
Gatea et al. (2015, Published Online: Oct. 14, 2014, Food Anal. Methods, DOI 10.1007/s12161-014-0018-1) {herein Gatea} (Year: 2014).*
International Search Report.
The first Office Action of the priority CN application.

(Continued)

*Primary Examiner* — Paul J Holland
*Assistant Examiner* — Erica Nicole Jones-Foster
(74) *Attorney, Agent, or Firm* — J.C. PATENTS

(57) ABSTRACT

A *Lactobacillus paracasei* and uses thereof. The *Lactobacillus paracasei* has a deposit number of CGMCC No. 14813. The *Lactobacillus paracasei* can be used for increasing the amount of an organic acid in a raw material. The *Lactobacillus paracasei* can be used for fermenting the raw material, where the raw material can be selected from at least one of fruits, which can increase the content of the organic acid in a fermented product.

4 Claims, No Drawings

(56) References Cited

OTHER PUBLICATIONS

NPL1: "Isolation and Identification of Predominant Microbes from Fruit and Vegetable Enzymes during Different Fermentation Process", China Food additives, No. 7, pp. 71-77, Jul. 31, 2018.
NPL2: "Selection of Strains for Lactic Acid Fermented Grape Juice and Flavor Analysis", Journal of Food Science and Technology, vol. 31, No. 3, pp. 34-38, May 31, 2013.
The Notice of Allowance of the priority CN application.
The first Office Action of the priority CN application No. 201910008854.7.
NPL1: "Progress in function characterization and application of Lactobacillus paracasei", Chinese Journal of Bioprocess Engineering, vol. 16, No. 4, pp. 1-7, Jul. 2018.

* cited by examiner

LACTOBACILLUS PARACASEI AND USES THEREOF

CROSS-REFERENCE TO RELATED APPLICATION

This application is a continuation of International Application No. PCT/CN2019/076376, filed on Feb. 27, 2019, which claims priority to Chinese Patent Application No. 201910008854.7, filed on Jan. 4, 2019. The disclosures of the aforementioned applications are hereby incorporated by reference in their entireties.

TECHNICAL FIELD

The present disclosure relates to Lactic acid bacteria and, in particular, to a *Lactobacillus paracasei* and uses thereof.

BACKGROUND

Organic acid is an acid with carboxyl groups contained in molecules, which widely exists in the bodies of animals, plants and microorganisms, and mainly includes lactic acid, acetic acid, propionic acid, butyric acid, malic acid, tartaric acid, oxalic acid, citric acid, and so on. Many kinds of organic acid can directly participate in a biochemical reaction, some of which have antibacterial, anti-inflammatory, antiviral, antimutagenic and anticancer effects, and the like; some of which can increase the amount of blood flow of coronary arteries, inhibit the formation of lipid peroxide in brain tissues, soften blood vessels, and promote the absorption of calcium and iron elements; and some other of which have the functions of helping gastric juice to digest fats and proteins, preventing diseases, and promoting metabolism, thereby benefiting to human health.

Lactic acid bacteria (LAB) are a general term of a kind of bacteria that can produce a large amount of lactic acid by using fermentable carbohydrates. A large number of studies have shown that Lactic acid bacteria can regulate the normal bacteria flora in gastrointestinal tract, maintain microecological balance, improve food digestibility and biological value, reduce serum cholesterol, control endotoxin, inhibit the growth and reproduction of spoilage bacteria and the production of spoilage products in the intestinal tract, produce nutrients, and stimulate tissue development, thus exerting effects on the nutritional status, physiological function, cell infection, drug effect, toxic reaction, immune reaction, tumorigenesis, aging process and sudden emergency response of an organism.

The Lactic acid bacteria produce organic acid and other substances through fermentation, to thus exert its special physiological functions. The Lactic acid bacteria can decompose lactose into glucose and galactose, and the glucose is transformed into small molecular compounds, such as lactic acid, by fermentation, which is helpful for the development of children's brain tissue and nervous system. The Lactic acid bacteria have phosphoprotease, which can decompose α-casein into fine cheese lipopeptides and amino acids, thus improving the digestion and absorption rates of proteins. Fermentation of the Lactic acid bacteria can make some fat to be slightly degraded, which facilitates the digestion and can increase the contents of free fatty acid and volatile fatty acid in milk. The Lactic acid bacteria consume some vitamins during metabolism, and also synthesize B vitamins such as folic acid. The organic acid produced after the fermentation of the Lactic acid bacteria can improve the utilization rate of calcium, phosphorus, iron, and other elements, promote the absorption of iron and VD, and have a strong bacteriostatic effect.

At present, the content of the organic acid in plants and microorganisms is relatively lower, so that a method that can increase the content of the organic acid is desirable.

SUMMARY

The present disclosure provides a *Lactobacillus paracasei* and uses thereof, the content of an organic acid in a fermented product can be improved by fermenting a raw material with the *Lactobacillus paracasei*.

The present disclosure provides a *Lactobacillus paracasei* with a deposit number of CGMCC No. 14813.

The phenotypic characteristics of the *Lactobacillus paracasei* (CGMCC No. 14813) of the present disclosure are: G+, rod-shaped, round colony, creamy color, wet surface, and neat edge.

The *Lactobacillus paracasei* (CGMCC No. 14813) of the present disclosure is independently obtained by separating and screening from naturally fermented fruit and vegetable enzymes by a culturable method, and the taxonomic status is determined by using 16S rRNA gene sequence and pheS gene phylogenetic analysis in combination with phenotypic characteristics.

The growth conditions of the *Lactobacillus paracasei* (CGMCC No. 14813) of the present disclosure can be conventional conditions, the growth conditions, for example, can be: a growth temperature of 30-37° C., facultative anaerobic and a growth time of 24-48 hours.

The *Lactobacillus paracasei* (CGMCC No. 14813) of the present disclosure can ferment to produce an organic acid, therefore, it can be used for related uses.

The present disclosure also provides a use of the above *Lactobacillus paracasei* (CGMCC No. 14813) in the production of an organic acid.

According to the present disclosure, the use ways of the *Lactobacillus paracasei* (CGMCC No. 14813) in the production of the organic acid are not strictly limited, and fermented products containing the organic acid can be produced, and the organic acid can be extracted from the fermented products as required to provide downstream applications.

The present disclosure also provide a method for producing a fermented product, which uses the *Lactobacillus paracasei* (CGMCC No. 14813) described above for fermenting a raw material.

According to the present disclosure, the raw material is not strictly limited, as long as the raw material is beneficial for the *Lactobacillus paracasei* (CGMCC No. 14813) to produce the organic acid.

Specifically, the raw material can be selected from at least one of a fruit and a medicinal and edible homologous raw material. Furthermore, the fruit includes grapes, blueberries, raspberries, pears, and the like, and the medicinal and edible homologous raw material includes mulberries, lilies, dark plums and lotus seeds, and the like.

When the *Lactobacillus paracasei* (CGMCC No. 14813) is used for fermenting the raw material, fermented culture mediums and fermentation conditions are not strictly limited, as long as they are beneficial for the *Lactobacillus paracasei* (CGMCC No. 14813) to produce the organic acid.

In a specific embodiment of the present disclosure, a method for producing a fermented product can include the following steps:

juicing and mixing the raw material to obtain a raw material juice;

adding 0-80 g of a carbon source, 3-8 g of a nitrogen source, 1-3 g of an inorganic salt and 8-12 g of calcium carbonate to the raw material juice per liter, and then adjusting pH value to 5.5-6.8 to obtain a fermented culture medium;

inoculating the *Lactobacillus paracasei* to the fermented culture medium at 0.5-1.5% (v/v) for fermenting to obtain a fermented product.

In the present disclosure, the raw material can be juiced by using conventional methods to obtain a raw juice of the raw material. In addition, the raw juice of the raw material can be subjected to size mixing according to actual needs. Specifically, the size mixing can be carried out by using distilled water, where a volume ratio of the raw juice of the raw material to the distilled water can be controlled to be 1:(1-5), so that the raw material juice is obtained.

According to the present disclosure, the carbon source, the nitrogen source, and the inorganic salt are not strictly limited, as long as they are suitable for the *Lactobacillus paracasei* to produce the organic acid. Specifically, the carbon source can be at least one of sucrose, glucose, and maltose, the nitrogen source can be at least one of peptone, beef extract, ammonium chloride, ammonium nitrate, and potassium nitrate, and the inorganic salt can be at least one of manganese sulfate, dipotassium hydrogen phosphate, and potassium dihydrogen phosphate.

Furthermore, calcium carbonate can also be added to the raw material juice. With the progress of fermentation, strains continuously produce the acid, which will reduce pH, and may affect the growth and fermentation of the strains; therefore, calcium carbonate can be added as needed to serve the purpose of consuming $H^+$ and stabilizing pH.

Same as conventional fermentation processes, the process for producing the organic acid by using *Lactobacillus paracasei* according to the present disclosure also includes the operations of activating strains, preparing a seed solution, and inoculating the seed solution to the fermented culture medium to carry out fermentation operation. According to the present disclosure, the fermentation conditions are not strictly limited, as long as the fermentation conditions are suitable for the *Lactobacillus paracasei* to produce the organic acid. Specifically, the fermentation temperature can be 20-35° C., the rotation speed can be 60-150 r/min, and the fermentation period can be 7-30 days. The research of the inventor shows that, compared with similar strains, such as *Lactobacillus paracasei* standard strain ATCC 25302, the *Lactobacillus paracasei* (CGMCC No. 14813) provided by the present disclosure not only increases the content of the organic acid in a fermented product, but also reduces the required inoculation amount, and shows obvious advantages in production efficiency and cost.

The present disclosure also provides a fermented product, which is produced according to any of the above-mentioned methods for producing a fermented product.

The fermented product of the present disclosure contains an organic acid. Furthermore, the organic acid includes at least one of lactic acid, acetic acid, propionic acid, butyric acid, malic acid, tartaric acid, oxalic acid, and citric acid.

The *Lactobacillus paracasei* described in the present disclosure has been preserved in the China General Microbiological Culture Collection Center (CGMCC for short) on Oct. 16, 2017, and its address is No. 3, No. 1 Courtyard, Beichen West Road, Chaoyang District, Beijing, and the deposit number is CGMCC No. 14813.

The *Lactobacillus paracasei* (CGMCC No. 14813) provided by the present disclosure can ferment to produce an organic acid, and when the *Lactobacillus paracasei* is used for fermenting a raw material, the content of the organic acid in a fermented product can be increased.

DESCRIPTION OF EMBODIMENTS

In order to make the objectives, technical solutions, and advantages of the present disclosure clearer, the technical solutions in embodiments of the present disclosure will be described clearly and comprehensively in combination with the embodiments of the present disclosure. Apparently, the described embodiments are a part rather than all embodiments of the present disclosure. Based on the embodiments of the present disclosure, all other embodiments obtained by those ordinary skilled in the art without creative effort fall within the protection scope of the present disclosure.

Example 1

I. Preparation of a Culture Medium

1) Basic Culture Medium 10.0 g of casein peptone, 10.0 g of beef extract, 5.0 g of yeast powder, 5.0 g of glucose, 5.0 g of sodium acetate, 2.0 g of diammonium citrate, 1.0 g of tween 80, 2.0 g of $K_2HPO_4$, 0.2 g of $MgSO_4 \cdot 7H_2O$, 0.05 g of $MnSO_4 \cdot H_2O$, and 10.0 g of $CaCO_3$ are dissolved in 1 L of distilled water, and the pH value is adjusted to 6.8, to obtain a basic culture medium (20 g of agar is added when a solid culture medium is prepared).

2) Fermented Culture Medium grapes are juiced to obtain a grape raw juice; distilled water is added to the grape raw juice for size mixing, and a volume ratio of the grape raw juice to distilled water is controlled to be 1:1 to obtain a grape juice.

40 g of glucose, 6 g of peptone, 2.5 g of manganese sulfate, and 10.0 g of $CaCO_3$ are added to 1 L of the above grape juice, and the pH value is adjusted to about 6.8 to obtain a fermented culture medium.

II. Fermentation

1) Activation of Strains

*Lactobacillus paracasei* strains (CGMCC No. 14813) stored on an inclined plane are inoculated into the above solid basic culture medium, and then subjected to standing and culturing for about 24 hours under an anaerobic condition to obtain activated strains.

2) Preparation of a Seed Solution the above activated strains are inoculated into the above liquid basic culture medium, and then subjected to standing and culturing for about 24 h under the anaerobic condition to obtain a seed solution.

3) Fermentation according to the inoculation amount of 0.8% (v/v), the above seed solution is inoculated into the above fermented culture medium for fermenting and culturing, and the fermentation temperature is controlled to be at about 35° C., the rotation speed is controlled to be about 150 r/min, and the fermentation period is controlled to be about 7 days, to obtain a grape fermented product.

The organic acid in the grape fermented product is detected by adopting the agricultural industry standard NY/T 2277-2012 method of the People's Republic of China, and the results are shown in Table 1.

Example 2

I. Preparation of a Culture Medium

1) Basic Culture Medium 8.0 g of casein peptone, 12.0 g of beef extract, 4.0 g of yeast powder, 6.0 g of glucose, 6.0 g of sodium acetate, 1.0 g of diammonium citrate, 1.5 g of tween 80, 3.0 g of $K_2HPO_4$, 0.1 g of $MgSO_4·7H_2O$, 0.1 g of $MnSO_4·H_2O$, and 8.0 g of $CaCO_3$ are dissolved in 1 L of distilled water, and the pH value is adjusted to 6.0, to obtain a basic culture medium (20 g of agar is added when a solid culture medium is prepared).

2) Fermented Culture Medium blueberries are juiced to obtain a blueberry raw juice; distilled water is added to the blueberry raw juice for size mixing, and a volume ratio of the blueberry raw juice to distilled water is controlled to be 1:2 to obtain a blueberry juice.

60 g of glucose, 4 g of peptone, 2.0 g of manganese sulfate, and 8.0 g of $CaCO_3$ are added to 1 L of the above blueberry juice, and the pH value is adjusted to about 6.0 to obtain a fermented culture medium.

II. Fermentation

1) Activation of Strains

*Lactobacillus paracasei* strains (CGMCC No. 14813) stored on an inclined plane are inoculated into the above solid basic culture medium, and then subjected to standing and culturing for about 18 hours under an anaerobic condition to obtain activated strains.

2) Preparation of a Seed Solution the above activated strains are inoculated into the above liquid basic culture medium, and then subjected to standing and culturing for about 24 h under the anaerobic condition to obtain a seed solution.

3) Fermentation according to the inoculation amount of 0.8% (v/v), the above seed solution is inoculated into the above fermented culture medium for fermenting and culturing, and the fermentation temperature is controlled to be at about 30° C., the rotation speed is controlled to be about 120 r/min, and the fermentation period is controlled to be about 10 days, to obtain a blueberry fermented product.

The organic acid in the blueberry fermented product is detected by adopting the agricultural industry standard NY/T 2277-2012 method of the People's Republic of China, and the results are shown in Table 2.

Example 3

I. Preparation of a Culture Medium

1) Basic Culture Medium 12.0 g of casein peptone, 8.0 g of beef extract, 6.0 g of yeast powder, 4.0 g of glucose, 4.0 g of sodium acetate, 3.0 g of diammonium citrate, 0.5 g of tween 80, 1.0 g of $K_2HPO_4$, 0.3 g of $MgSO_4·7H_2O$, 0.01 g of $MnSO_4·H_2O$, and 12.0 g of $CaCO_3$ are dissolved in 1 L of distilled water, and the pH value is adjusted to 6.5, to obtain a basic culture medium (20 g of agar is added when a solid culture medium is prepared).

2) Fermented Culture Medium raspberries are juiced to obtain a raspberry raw juice; distilled water is added to the raspberry raw juice for size mixing, and a the volume ratio of the raspberry raw juice to distilled water is controlled to be 1:3 to obtain a raspberry juice.

20 g of maltose, 5 g of ammonium chloride, 2 g of potassium dihydrogen phosphate, and 12.0 g of $CaCO_3$ to 1 L of the above raspberry juice, and the pH value is adjusted to about 6.5 to obtain a fermented culture medium.

II. Fermentation

1) Activation of Strains

*Lactobacillus paracasei* strains (CGMCC No. 14813) stored on an inclined plane are inoculated into the above solid basic culture medium, and then subjected to standing and culturing for about 18 hours under an anaerobic condition to obtain activated strains.

2) Preparation of a Seed Solution the above activated strains are inoculated into the above liquid basic culture medium, and then subjected to standing and culturing for about 24 h under the anaerobic condition to obtain a seed solution.

3) Fermentation according to the inoculation amount of 1% (v/v), the above seed solution is inoculated into the above fermented culture medium for fermenting and culturing, and the fermentation temperature is controlled to be at about 32° C., the rotation speed is controlled to be about 150 r/min, and the fermentation period is controlled to be about 15 days, to obtain a raspberry fermented product.

The organic acid in the raspberry fermented product is detected by adopting the agricultural industry standard NY/T 2277-2012 method of the People's Republic of China, and the results are shown in Table 3.

Example 4

I. Preparation of a Culture Medium

1) Basic Culture Medium 10.0 g of casein peptone, 10.0 g of beef extract, 5.0 g of yeast powder, 5.0 g of glucose, 5.0 g of sodium acetate, 2.0 g of diammonium citrate, 1.0 g of tween 80, 2.0 g of $K_2HPO_4$, 0.2 g of $MgSO_4·7H_2O$, 0.05 g of $MnSO_4·H_2O$, and 10.0 g of $CaCO_3$ are dissolved in 1 L of distilled water, and the pH value is adjusted to 6.8, to obtain a basic culture medium (20 g of agar is added when a solid culture medium is prepared).

2) Fermented Culture Medium pears are juiced to obtain a pear raw juice; distilled water is added to the pear raw juice for size mixing, and a volume ratio of the pear raw juice to distilled water is controlled to be 1:1 to obtain a pear juice.

10 g of sucrose, 4 g of ammonium nitrate, 1 g of manganese sulfate, 1 g of dipotassium hydrogen phosphate, and 10.0 g of $CaCO_3$ are added to 1 L of the above pear juice, and the pH value is adjusted to about 6.8 to obtain a fermented culture medium.

II. Fermentation

1) Activation of Strains

*Lactobacillus paracasei* strains (CGMCC No. 14813) stored on an inclined plane are inoculated into the above solid basic culture medium, and then subjected to standing and culturing for about 24 hours under an anaerobic condition to obtain activated strains.

2) Preparation of a Seed Solution the above activated strains are inoculated into the above liquid basic culture medium, and then subjected to standing and culturing for about 24 h under the anaerobic condition to obtain a seed solution.

3) Fermentation according to the inoculation amount of 0.8% (v/v), the above seed solution is inoculated into the above fermented culture medium for fermenting and culturing, and the fermentation temperature is controlled to be at about 35° C., the rotation speed is controlled to be about 150 r/min, and the fermentation period is controlled to be about 7 days, to obtain a pear fermented product.

The organic acid in the pear fermented product is detected by adopting the agricultural industry standard NY/T 2277-2012 method of the People's Republic of China, and the results are shown in Table 4.

Comparative Examples 1-4

*Lactobacillus paracasei* standard strain ATCC 25302 is taken as a control in Comparative Examples 1-4, the rest are the same as those in Examples 1-4, except that *Lactobacillus paracasei* strain CGMCC No. 14813 in Examples 1-4 is replaced with the *Lactobacillus paracasei* standard strain ATCC 25302, and the inoculation amount is changed according to the following description.

In Comparative Example 1, according to the inoculation amount of 3% (v/v), a seed solution is inoculated into a fermented culture medium for fermenting and culturing.

In Comparative Example 2, according to the inoculation amount of 5% (v/v), a seed solution is inoculated into a fermented culture medium for fermenting and culturing.

In Comparative Example 3, according to the inoculation amount of 1% (v/v), a seed solution is inoculated into a fermented culture medium for fermenting and culturing.

In Comparative Example 4, according to the inoculation amount of 2% (v/v), a seed solution is inoculated into a fermented culture medium for fermenting and culturing.

The contents of organic acids in fermented products of Comparative Example 1-4 are detected by the same method, and the detection results are shown in Tables 1 to 4 respectively.

TABLE 1

Detection results of organic acids in grape fermented products of Example 1 and Comparative Example 1

| Sample | Organic acid (g/L) | | | | | | | | Total content of the organic acid (g/L) |
|---|---|---|---|---|---|---|---|---|---|
| | Lactic acid | Acetic acid | Propanoic acid | Butyric acid | Malic acid | Tartaric acid | Oxalic acid | Citric acid | |
| Grape Juice | 0.031 | / | 0.020 | / | 2.253 | 3.394 | 0.276 | 0.133 | 6.107 |
| Example 1 Fermented product | 18.342 | 0.512 | 0.135 | 0.009 | 0.093 | 1.669 | 0.942 | 0.103 | 21.805 |
| Comparative Example 1 Fermented product | 12.395 | 0.490 | 0.067 | 0.025 | 0.037 | 0.301 | 0.071 | 0.103 | 13.489 |

Note:
"/" means not detected.

TABLE 2

Detection results of organic acids in blueberry fermented products of Example 2 and Comparative Example 2

| Sample | Organic acid (g/L) | | | | | | | | Total content of the organic acid (g/L) |
|---|---|---|---|---|---|---|---|---|---|
| | Lactic acid | Acetic acid | Propanoic acid | Butyric acid | Malic acid | Tartaric acid | Oxalic acid | Citric acid | |
| Blueberry juice | / | / | / | / | 0.192 | 0.055 | 0.145 | 3.134 | 3.526 |
| Example 2 Fermented product | 10.411 | 0.170 | 0.068 | 0.020 | 0.058 | 0.053 | 0.331 | / | 11.112 |
| Comparative Example 2 Fermented product | 6.943 | 0.490 | 0.074 | 0.056 | 0.040 | 0.664 | 0.354 | 0.081 | 8.703 |

Note:
"/" means not detected.

TABLE 3

Detection results of organic acids in raspberry fermented products of Example 3 and Comparative Example 3

| Sample | Organic acid (g/L) | | | | | | | | Total content of the organic acid (g/L) |
|---|---|---|---|---|---|---|---|---|---|
| | Lactic acid | Acetic acid | Propanoic acid | Butyric acid | Malic acid | Tartaric acid | Oxalic acid | Citric acid | |
| Raspberry juice | / | 0.224 | / | / | 0.057 | / | 0.072 | 1.540 | 1.893 |
| Example 3 Fermented product | 3.250 | 0.939 | 0.160 | 0.035 | 0.388 | 1.430 | 0.487 | 0.119 | 6.807 |
| Comparative Example 3 Fermented product | 2.048 | 0.166 | 0.352 | 0.026 | 0.062 | 0.355 | 0.169 | 0.152 | 3.330 |

Note:
"/" means not detected.

TABLE 4

Detection results of organic acids in pear fermented products of Example 4 and Comparative Example 4

| Sample | Organic acid (g/L) | | | | | | | | Total content of the organic acid (g/L) |
|---|---|---|---|---|---|---|---|---|---|
| | Lactic acid | Acetic acid | Propanoic acid | Butyric acid | Malic acid | Tartaric acid | Oxalic acid | Citric acid | |
| Pear juice | / | / | / | / | 1.33 | 0.057 | 0.217 | 1.041 | 2.645 |
| Example 4 Fermented product | 4.637 | 0.474 | 0.115 | 0.012 | 0.593 | 0.010 | 0.023 | 0.067 | 5.930 |
| Comparative Example 4 Fermented product | 2.358 | 0.090 | 0.069 | 0.038 | 1.039 | / | 0.056 | 0.093 | 3.744 |

Note:
"/" means not detected.

The results in Tables 1 to 4 show that:
compared with the unfermented raw juices and the fermented products fermented by *Lactobacillus paracasei* standard strain ATCC 25302, the content of the organic acid in the fermented products fermented by *Lactobacillus paracasei* (CGMCC No. 14813) of the present disclosure is significantly increased.

Finally, it should be noted that the foregoing respective embodiments are merely intended for describing the technical solutions of the present disclosure other than limiting the present disclosure. Although the present disclosure is described in detail with reference to the foregoing respective embodiments, those ordinary skilled in the art should understand that the technical solutions described in the foregoing respective embodiments can still be modified, or some or all of the technical features can be equivalently substituted; however, these modifications or substitutions do not make the essence of the corresponding technical solutions deviate from the scope of the technical solutions of respective embodiments of the present disclosure.

What is claimed is:

1. A method for producing an organic acid, the method comprising: inoculating a raw material with a *Lactobacillus paracasei* and fermenting said raw material and said *Lactobacillus paracasei* to produce said organic acid, wherein said fermenting is at a temperature of 20-35° C., a rotation speed of 60-150 r/min, and a fermentation period of 7-30 days; wherein said *Lactobacillus paracasei* has a deposit number of CGMCC No. 14813, wherein said organic acid produced by said *Lactobacillus paracasei* with the deposit number of CGMCC No. 14813 has an increased total content of an organic acid, as compared to an organic acid produced by an *Lactobacillus paracasei* strain ATCC 25302, and wherein said organic acid comprises at least three of lactic acid, acetic acid, propionic acid, butyric acid, malic acid, tartaric acid, oxalic acid, and citric acid.

2. The method for producing the organic acid of claim 1, wherein the raw material is selected from at least one of a fruit and a medicinal and edible homologous raw material.

3. The method for producing the organic acid of claim 2, wherein the fruit comprises grapes, blueberries, raspberries, and pears, and the medicinal and edible homologous raw material comprises mulberries, lilies, dark plums, and lotus seeds.

4. The method for producing the organic acid of claim 1, further comprising:

juicing and mixing the raw material to obtain a raw material juice;

adding 0-80 g of a carbon source, 3-8 g of a nitrogen source, 1-3 g of an inorganic salt and 8-12 g of calcium carbonate to the raw material juice per liter, and then adjusting pH value to 5.5-6.8 to obtain a fermented culture medium;

inoculating the *Lactobacillus paracasei* with the deposit number of CGMCC No. 14813 into the fermented culture medium at a concentration of 0.5-1.5% (v/v) for fermenting to produce said organic acid.

* * * * *